United States Patent
Berbeco et al.

(10) Patent No.: US 10,625,100 B2
(45) Date of Patent: Apr. 21, 2020

(54) REAL-TIME MARGIN ADAPTATION

(71) Applicant: BRIGHAM AND WOMEN'S HOSPITAL, INC., Boston, MA (US)

(72) Inventors: Ross Berbeco, Cambridge, MA (US); Joerg Rottmann, Brookline, MA (US)

(73) Assignee: BRIGHAM AND WOMEN'S HOSPITAL, INC., Boston, MA (US)

( * ) Notice: Subject to any disclaimer, the term of this patent is extended or adjusted under 35 U.S.C. 154(b) by 97 days.

(21) Appl. No.: 15/306,882

(22) PCT Filed: Apr. 27, 2015

(86) PCT No.: PCT/US2015/027709
§ 371 (c)(1),
(2) Date: Oct. 26, 2016

(87) PCT Pub. No.: WO2015/167980
PCT Pub. Date: Nov. 5, 2015

(65) Prior Publication Data
US 2017/0050051 A1    Feb. 23, 2017

Related U.S. Application Data

(60) Provisional application No. 61/985,121, filed on Apr. 28, 2014.

(51) Int. Cl.
*A61N 5/10* (2006.01)
*A61B 5/05* (2006.01)
*A61B 5/055* (2006.01)

(52) U.S. Cl.
CPC ............. *A61N 5/1064* (2013.01); *A61B 5/05* (2013.01); *A61B 5/055* (2013.01); *A61N 5/1037* (2013.01);

(Continued)

(58) Field of Classification Search
CPC .... A61N 5/103; A61N 5/1031; A61N 5/1036; A61N 5/1037; A61N 5/1038;
(Continued)

(56) References Cited

U.S. PATENT DOCUMENTS

| 7,835,493 | B2 | 11/2010 | Keall |
| 8,340,247 | B2 | 12/2012 | Keall |
| 2005/0111621 | A1* | 5/2005 | Riker .................. A61N 5/1031 378/65 |
| 2005/0151071 | A1 | 7/2005 | Nilsson |
| 2005/0201516 | A1 | 9/2005 | Ruchala et al. |

(Continued)

OTHER PUBLICATIONS

The International Search Report and Written Opinion as dated Jul. 28, 2015 for International Application No. PCT/US2015/027709.

(Continued)

*Primary Examiner* — Carrie R Dorna
(74) *Attorney, Agent, or Firm* — Quarles & Brady LLP

(57) ABSTRACT

Systems and methods directed to real-time treatment margin adaptation based on in-treatment imaging are provided. The system and method may utilize the potential of motion mitigation techniques such as couch tracking, DMLC, beam tracking, and the like to freeze tumor motion within the treatment aperture. A standard internal target volume (ITV) based margin plan and a minimum margin plan is created for the patient. The minimum margin plan assumes frozen intrafractional tumor motion. Depending on tumor location confidence in the motion mitigation technique, MLC leaf positions can be interpolated between the two plans to adjust margins during treatment delivery. If motion mitigation fails, the plan can be disabled resulting in the delivery of the current clinical standard of care. Dynamic aperture tracking may be employed with an electronic portal imaging device as the in-treatment imaging modality.

21 Claims, 5 Drawing Sheets

(52) U.S. Cl.
CPC ......... *A61N 5/1049* (2013.01); *A61N 5/1067* (2013.01); *A61N 5/1075* (2013.01); *A61N 2005/1054* (2013.01); *A61N 2005/1055* (2013.01); *A61N 2005/1061* (2013.01); *A61N 2005/1076* (2013.01)

(58) Field of Classification Search
CPC .. A61N 5/1039; A61N 5/1045; A61N 5/1047; A61N 5/1048; A61N 5/1049; A61N 5/1071; A61N 2005/1041; A61N 2005/1051; A61N 2005/1052; A61N 2005/1055; A61N 2005/1058
See application file for complete search history.

(56) References Cited

U.S. PATENT DOCUMENTS

| | | |
|---|---|---|
| 2007/0244386 A1 | 10/2007 | Steckner et al. |
| 2008/0081991 A1* | 4/2008 | West ................ A61N 5/1031 600/425 |
| 2011/0044429 A1 | 2/2011 | Takahashi et al. |
| 2011/0208055 A1 | 8/2011 | Dalal et al. |
| 2014/0005464 A1 | 1/2014 | Bharat et al. |
| 2014/0107390 A1 | 4/2014 | Brown et al. |

OTHER PUBLICATIONS

Court, Le et al, "Use of a realistic breathing lung phantom to evaluate dose delivery errors.", Med Phys 37(11), 5850-5857, (2010).

Keall, Paul J., et al. "The management of respiratory motion in radiation oncology report of AAPM Task Group 76 a." Medical physics 33.10 (2006): 3874-3900.

Keall, PJ, "Geometric accuracy of a real-time target tracking system with dynamic multi-leaf collimator tracking system.", Int J Radiat Oncol Biol Phys 65(5), 1579-1584. (2006).

Rottmann, J et al, "Real-time soft tissue motion estimation for lung tumors during radiotherapy delivery", Medical Physics 40(9), 091713, (2013).

Rottmann, J., et al. "A multi-region algorithm for markerless beam's-eye view lung tumor tracking." Physics in Medicine & Biology 55.18 (2010): 5585.

Rottmann, J., et al. "Markerless EPID image guided dynamic multi-leaf collimator tracking for lung tumors." Physics in Medicine & Biology 58.12 (2013): 4195.

Rottmann, J., et al. Real-Time Markerless Tumor Tracking with MV Imaging and a Dynamic Multi-Leaf Collimator (DMLC) (Fifty-fourth annual meeting of the American Association of Physicists in Medicin, 2012) pp. 3890-3890.

Rottmann, J. et al. "Using an external surrogate for predictor model training in real-time motion management of lung tumors." Medical physics 41.12 (2014): 121706.

Shirato, Hiroki, et al. "Four-dimensional treatment planning and fluoroscopic real-time tumor tracking radiotherapy or moving tumor." International Journal of Radiation Oncology* Biology* Physics 48.2 (2000): 435-442.

Van Herk, M. (Jan. 2004). Errors and margins in radiotherapy. In Seminars in radiation oncology (vol. 14, No. 1, pp. 52-64). WB Saunders.

* cited by examiner

REAL-TIME MARGIN ADAPTATION

CROSS-REFERENCE TO RELATED APPLICATIONS

This application represents is a 371 application of PCT/US2015/027709 filed Apr. 27, 2015, which claims the benefit of, U.S. Provisional Patent Application Ser. No. 61/985,121, filed on Apr. 28, 2014, both of which are hereby incorporated herein by reference for all purposes.

STATEMENT REGARDING FEDERALLY SPONSORED RESEARCH

NA

BACKGROUND

The present disclosure relates generally to systems and methods for use in radiotherapy treatment delivery. More particularly, the disclosure relates to systems and methods for real-time treatment margin adaptation during radiotherapy for moving tumors.

External beam radiation therapy is designed to selectively destroy tumor tissue by administering large, spatially-controlled doses of radiation to a subject. The "Rule of Thumb" for such procedures is that the dose delivered should be within ±5 percent of the planned dose and within ±5 mm of the planned position. The treatment process proceeds through a number of steps, beginning with a contoured dose prescription indicated by a radiation oncologist using a set of diagnostic images. A dosimetrist, with the aid of a treatment planning system (TPS), then determines the dose to be delivered from each of a set of beam geometries and incident angles. The TPS utilizes stored dosimetric information, which is typically obtained from measurements on phantoms, to deterministically calculate dose delivery. Once the treatment plan has been approved by the oncologist, the treatment regiment begins. Prior to radiation delivery, the subject is positioned as exactly as possible to match the position used for treatment planning. This includes the alignment of skin markers with room lasers and the acquisition of CT or x-ray images for registration with planning images using either intrinsic or extrinsic fiducial markers. Typically, kilovoltage (kV) imaging is performed using an on-board imaging device (OBI) or megavoltage (MV) imaging is performed using an electronic portal imaging device (EPID). Immobilization devices can also be used to further increase positioning accuracy and minimize movement during treatment. After proper measures are taken to ensure a subject accurately receives the planned treatment, the radiation dose is delivered, typically at a rate of approximately 400 to 600 cGy per minute.

During external beam radiotherapy, patient setup uncertainties, as well as intrafractional tumor motion, cause a blurring of the delivered dose distribution relative to the dose distribution simulated during treatment planning. A commonly implemented strategy to account for this effect in the treatment plan is to enlarge the treated volume by utilizing geometric safety margins. The margin size is estimated by evaluation of pre-treatment data (e.g., 4DCT) and/or population based data. However, this concept relies on assumptions regarding both setup uncertainties and tumor motion during treatment delivery. The tumor position may change during radiation delivery due to several factors, such as respiration, peristalsis, relaxation, and the like. Inaccurate estimations of either setup or tumor margin may lead to undesirable dose distributions, such as under-dosing the tumor or overdosing surrounding healthy tissue.

Various techniques have been developed over recent years to facilitate motion management for moving tumors, mainly with respect to respiration which can be responsible for large tumor motion amplitudes. Couch tracking and dynamic multi-leaf collimator tracking both have been shown to be viable options for "freezing" tumor motion with respect to the treatment beam.

However, previous feasibility studies have maintained static treatment margins, even when real-time information is available. It would therefore be desirable to have a system and method for accurately locating the target, and to adapt the treatment aperture based on real-time confidence in the localization. It would also be desirable to have a system and method that utilizes a technique that is applicable regardless of the chosen in-treatment imaging type (e.g., MRI, kV, MV, etc.) and motion mitigation technique, such as multi-leaf collimator (MLC) tracking, couch tracking, and the like.

SUMMARY

The present invention overcomes the aforementioned drawbacks by providing a system and method for facilitating real-time treatment margin modification in external beam radio therapy based on in-treatment imaging. In some embodiments, the application of real-time margin adaptation using MV imaging and dynamic MLC aperture tracking is provided. In addition, a localization failure mode response mechanism whereby, the geometric safety margins can be adapted based on tumor location information, is provided.

In accordance with one aspect of the disclosure, a method for real-time treatment margin modification for use in radiotherapy treatment of a tumor of a subject is provided. The method includes acquiring image data from the tumor of the subject using an imaging system. Using a processor in communication with the imaging system, the image data is processed. A first treatment plan having a first set of treatment margins based on an internal target volume (ITV) of the processed image data is generated. A second treatment plan having a second set of treatment margins based on a gross tumor volume (GTV) of the processed image data is generated. Next, a tracking confidence parameter dependent on at least one of target localization or motion mitigation is calculated. The first treatment plan is utilized when the tracking confidence parameter is below a first predetermined threshold. The second treatment plan is utilized when the tracking confidence parameter is above a second predetermined threshold. A treatment plan having a third set of treatment margins between the first set of treatment margins and the second set of treatment margins is utilized when the tracking confidence parameter is between the first predetermined threshold and the second predetermined threshold.

In accordance with another aspect of the disclosure, a system for real-time treatment margin modification for use in radiotherapy treatment of a tumor of a subject is provided. The system includes an imaging system configured to acquiring image data from the tumor of the subject. A processor is in communication with the imaging system and configured to generate a first treatment plan having a first set of treatment margins based on an internal target volume (ITV) of the processed image data. The processer is further configured to generate a second treatment plan having a second set of treatment margins based on a gross tumor volume (GTV) of the processed image data. A tracking confidence parameter dependent on at least one of target localization or motion mitigation is calculated. The first treatment plan is utilized when the tracking confidence parameter is below a first predetermined threshold. The second treatment plan is utilized when the tracking confidence parameter is above a second predetermined threshold. A treatment plan having a third set of treatment margins between the first set of treatment margins and the second set of treatment margins is utilized when the tracking confidence parameter is between the first predetermined threshold and the second predetermined threshold.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

The present disclosure provides a system and method for radiation dose verification that utilizes real-time treatment margin adaptation based on in-treatment imaging to reduce healthy tissue dose, while maintaining tumor coverage during therapeutic radiation delivery. The system and method may utilize the potential of motion mitigation techniques such as couch tracking, DMLC, beam tracking, and the like to freeze tumor motion within the treatment aperture. A standard internal target volume (ITV) based margin plan and a minimum margin plan is created for the patient. The minimum margin plan assumes frozen intrafractional tumor motion. Depending on tumor location confidence in the motion mitigation technique, MLC leaf positions can be interpolated between the two plans to adjust margins during treatment delivery. If motion mitigation fails, the plan can be disabled resulting in the delivery of the current clinical standard of care. Dynamic aperture tracking may be employed with an electronic portal imaging device as the in-treatment imaging modality. A 3D printed tumor model may be used as the target and moved along a patient breathing trajectory. To assess the radiation delivery, film measurements in the tumor reference frame, as well as electronic portal images, may be utilized.

Figure 1:
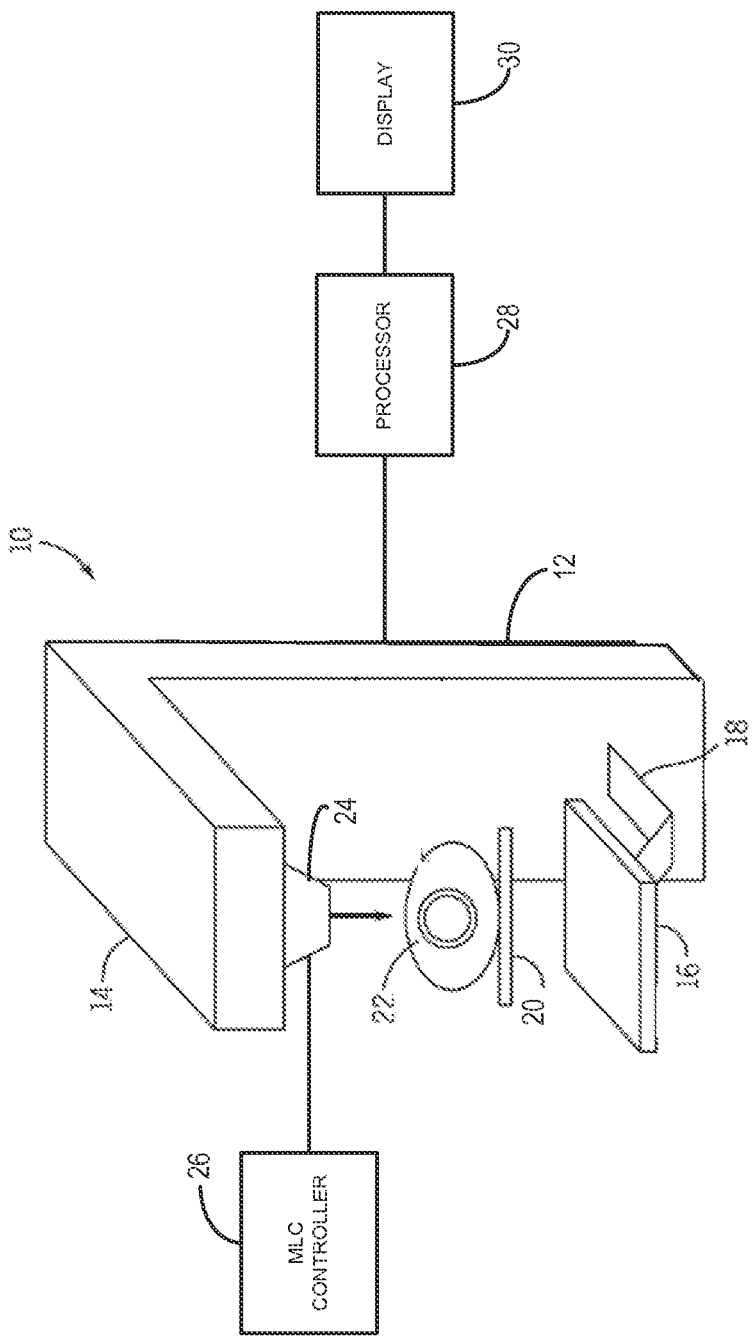
FIG. 1 is a schematic depiction of a radiotherapy system with dose verification in accordance with the present disclosure.

Referring to FIG. 1, a radiation therapy system 10 in accordance with the present disclosure is illustrated. The radiation therapy system 10 is designed to perform traditional radiotherapy and, also, dose verification. To this end, the radiation therapy system 10 includes a base 12 having a LINAC 14 supported by the base 12 and disposed above an EPID 16, which may be attached to the base 12 via a movable arm 18. A treatment table 20 onto which a subject 22 (or phantom) may be placed is disposed between the LINAC 14 and the EPID 16. In the head of the LINAC 14, a multi-leaf collimator (MLC) 24 may be positioned in the path of the radiation to define the contour or shape of the radiation beam profile. The MLC 24 comprises multiple leaves that move independently to form a beam shape. A MLC controller 26 controls the movement of each of the leaves. The radiation therapy system 10 is further connected to a processor 28 to deliver acquired data sets thereto, as will be described, and is configured to reconstruct an image indicating a radiation dose received by the subject 22 during a radiotherapy process. A display 30 may be provided to display the imaging data.

Figure 2:
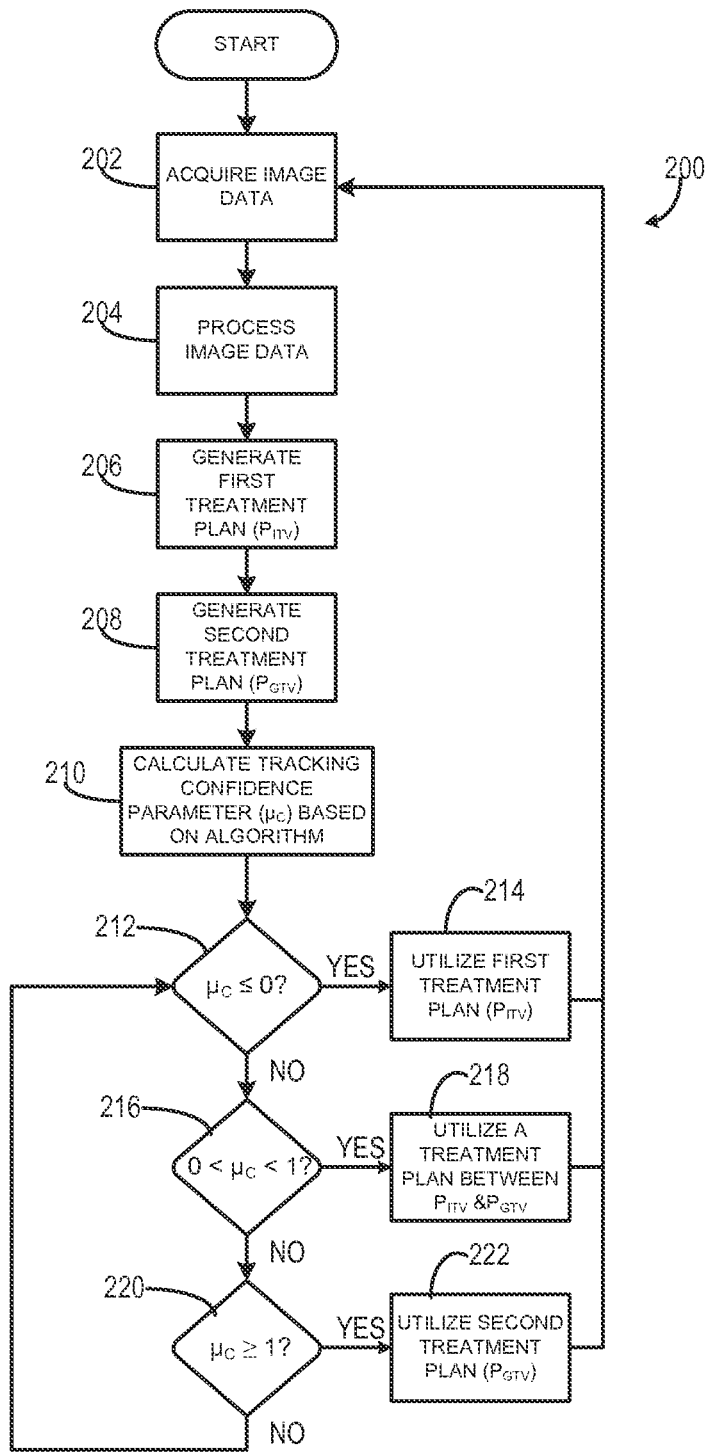
FIG. 2 is a flowchart setting forth exemplary steps associated with the process of providing radiotherapy treatment to a patient with real-time treatment margin modification.

Referring now to FIG. 2, a flow chart is provided setting forth exemplary steps 200 of a method to facilitate real-time treatment margin modification during external beam radiotherapy in accordance with the present disclosure. The method aims to shrink treatment margins during radiation delivery utilizing active motion mitigation techniques. To enable safe delivery of treatment plans with minimal margins, margins may be reduced in real-time depending on confidence in the motion mitigation and in-treatment tumor localization during treatment delivery. The process begins at process block 202 where medical image data is acquired from a patient typically using of a variety of imaging approaches, either for diagnostic or treatment purposes. For example, this can include use of computed tomography (CT) devices, magnetic resonance imaging (MRI) devices, positron emission tomography (PET) imaging devices, ultrasound (US) imaging devices, and so forth. Information obtained from imaging serves two main purposes in radiotherapy (RT). First, it is used to determine true three-dimensional positions and extent of targeted diseased tissues relative to adjacent critical structures or objects at risk (OARs), which typically have radiation dose toxicity constraints. Second, it is used to localize such targets and OARs, for example, during a daily treatment setup, in order to make any treatment adjustments prior to radiation delivery.

In general, CT images are the standard imaging modality utilized for treatment planning. In a simulation stage, a patient is immobilized and imaged with reference marks that establish specific coordinates, which may subsequently be reproduced in a treatment system during radiation delivery. The acquired images are then utilized in a planning stage to generate a treatment plan. In addition to CT images, other imaging modalities offer improved contrast and other useful information related to anatomical features and biological processes of normal and diseased tissues or structures. In particular, MRI is non-ionizing, and offers superior soft tissue contrast compared to CT, while providing a wide array of functional contrast forming mechanisms to characterize tumor physiology. However, in contrast to CT images, MR images lack electron density (ED) information, which is necessary for radiation dose calculations. Hence, such non- CT images need to be processed or synthesized to be "CT-like" in order to find use in RT planning and delivery.

Next, at process block 204, the image data may be processed or analyzed, for exampled, by the processor 28 of FIG. 1, to yield image information for use in treatment plan generation and delivery. The processed image data may be received, for example, from an imaging system or a data storage, and transferred to a planning system for use in generating a radiotherapy plan. Specifically, in the case that a plan is formulated for a first treatment, this process step typically includes the determination of beam or radiation source delivery techniques and arrangements based upon selected or determined planning aims. In certain planning approaches, this may include generating beam's eye-view displays, designing field shapes (blocks, multi-leaf collimators), determining beam modifiers (compensators, wedges) and determining beam or source weightings. Using contoured critical structures, performed either manually or using an automatic contouring tool, dose calculations may then performed based on selected algorithms or methodologies. Using set relative and absolute dose normalizations and dose prescriptions, a plan quality is then evaluated based on visual coverage comparisons, dose volume histogram analysis, and tumor control and normal tissue complication probabilities. Automated or semi-automated optimization tools may then allow for plan improvement based on the planning aims and tolerances.

Figure 3:
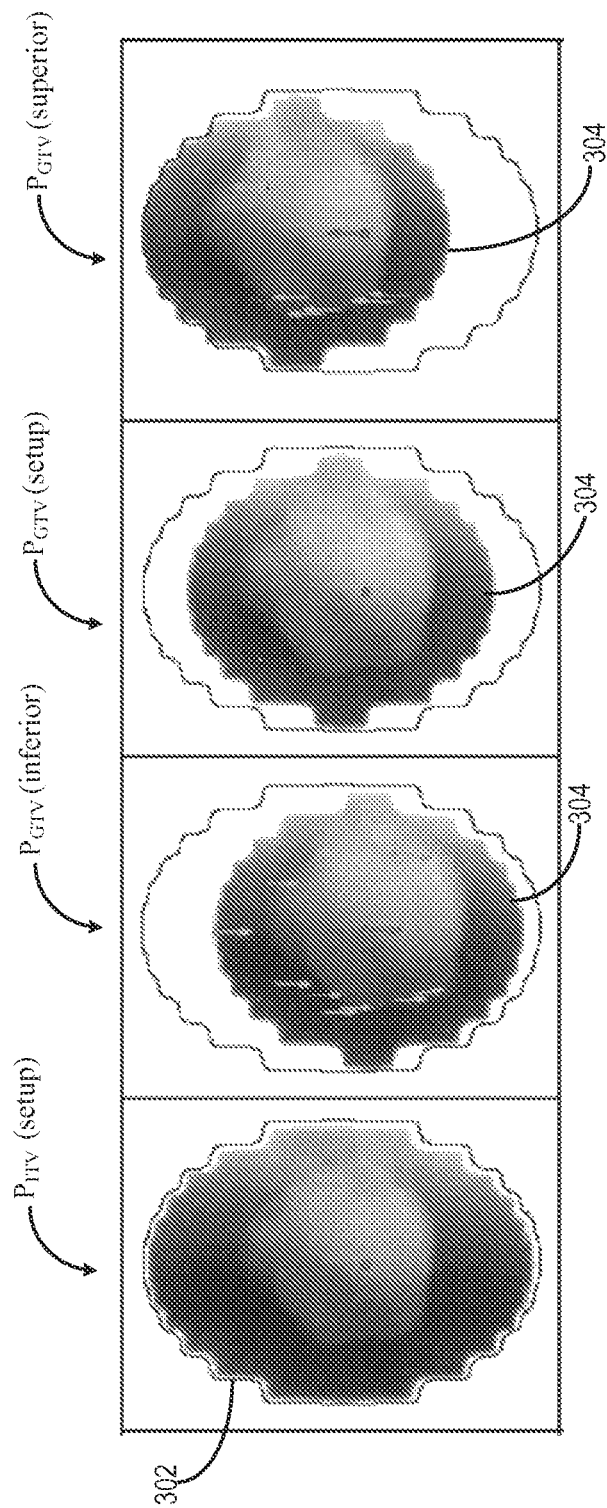
FIG. 3 shows example images of a first treatment plan ($P_{ITV}$) and a second treatment plan ($P_{GTV}$).

In some cases, generated plans may also involve taking into account intra-fractional motion, such as respiration motion, of target and critical structures. Thus, at process block 206, a first treatment plan ($P_{ITV}$) is generated for the patient that utilizes a 4D planning approach for intra-fractional motion based on 4DCT or 4D MR images, for example. The first treatment plan ($P_{ITV}$) may resemble the current standard of care regarding margin construction, as shown in FIG. 3. For example, the first treatment plan ($P_{ITV}$) may include an internal target volume (ITV) 302 that is contoured using pre-treatment imaging (e.g., 4DCT). The ITV 302 may encompass the full observed tumor motion range and may be expanded to the planning target volume (PTV) by a fixed margin (e.g., 1 mm plus motion range) to account for setup inaccuracies, target delineation inaccuracies, invisible microscopic decrease in the surrounding tissue to the lesion, and the like.

Next, at process block 208, a second treatment plan ($P_{GTV}$) is generated. The second treatment plan ($P_{GTV}$) may include minimal margins based on the assumption of negligible intrafractional target motion due to successful motion mitigation. For the second treatment plan/the minimal margin plan ($P_{GTV}$), intrafractional target motion may be assumed to be non-existent and only a gross tumor volume (GTV) 304 is contoured (e.g., on the end-of-exhale phase of a pre-treatment 4DCT), as shown in FIG. 3. Similar to the first treatment plan ($P_{ITV}$), the GTV 304 is expanded to a PTV. The GTV 304 is shown in FIG. 3 for the second treatment plan ($P_{GTV}$) with the tumor at an inferior, a setup and a superior position (the ITV 302 aperture outline is given for comparison).

Returning to FIG. 2, once the first treatment plan and the second treatment plan are generated at process blocks 206 and 208, respectively, a tracking confidence parameter $\mu_C$ may be calculated at process block 210. The tracking confidence parameter $\mu_C$ may be used to quantify a confidence level in the applied motion mitigation technique at each point in time, where $\mu_C(t) \in [-1, 1]$. Additionally, the tracking confidence parameter $\mu_C$ may describe a confidence level in the tracking accuracy of a soft tissue localization (STiL) algorithm. The calculation of the tracking confidence parameter $\mu_C(t)$ may depend on the selected options for target localization and motion mitigation.

The treatment plan may be adjusted between the ITV and the GTV leaf depending on the calculated tracking confidence parameter $\mu_C$. In addition, the tracking confidence parameter $\mu_C$ may be used to enable or disable motion mitigation and define a safely applicable margin reduction for each point in time. More specifically, at decision block 212, if the tracking confidence parameter $\mu_C$ is less than or equal to zero, the first treatment plan ($P_{ITV}$) will be utilized at process block 214, which as previously described, is the current standard of care. In one non-limiting example, a tracking confidence parameter $\mu_C$ less than zero may disable the motion mitigation in case of insufficient target localization accuracy, for example, due to failure of the image acquisition device or insufficient target visibility. If, however, the tracking confidence parameter $\mu_C$ is greater than or equal to zero, motion mitigation is enabled and margins are dynamically adapted between the first treatment plan ($P_{ITV}$) and the second treatment plan ($P_{GTV}$), as will be described in further detail below. Having the option to disable the motion mitigation without the need to load another plan manually may allow for more efficient radiation deliveries and reduce discomfort for the patient.

If, at decision block 212, the tracking confidence parameter $\mu_C$ is not less than or equal to zero, the processor determines whether the tracking confidence parameter $\mu_C$ has a value between zero and one at decision block 216. If the tracking confidence parameter $\mu_C$ has a value between zero and one at decision block 216, a treatment plan having margin between the first treatment plan ($P_{ITV}$) and the second treatment plan ($P_{GTV}$) my be utilized at process block 218. The margins may dynamically adapt between the first treatment plan ($P_{ITV}$) and the second treatment plan ($P_{GTV}$) by means of linear interpolation leaf positions weighted by $\mu_C$. For example, let $\ell(t) = (\ell_1(t), \ldots, \ell_n(t))^T$ be the vector of n collimator leaf positions and $\ell_{itv}$ and $\ell_{ptv}$ the leaf positions for the first treatment plan ($P_{ITV}$) and the second treatment plan ($P_{GTV}$), respectively. Then the current leaf positions are given by Eqn. (1) below:

$$\ell(t) = \ell_{itv} - \mu_C(t)(\ell_{itv} - \ell_{gtv}), \mu_C \geq 0 \qquad \text{Eqn. (1)}$$

The proposed concept may work analogously for treatment plans utilizing modulated leaf sequences, such as IMRT and VMAT, if the leaf positions $\ell_{ptv}$ and $\ell_{gtv}$ are replaced by their time dependent counterparts $\ell_{ptv}(t)$ and $\ell_{gtv}(t)$. However, due to the reduced target visibility from leafs moving through the treatment aperture, other imaging inputs (e.g., using fiducial markers or kV imaging) may be used.

If, however, the tracking confidence parameter $\mu_C$ is not between zero and one at decision block 216, the processor determines whether the tracking confidence parameter $\mu_C$ has a value greater than or equal to one at decision block 220. If the tracking confidence parameter $\mu_C$ has a value greater than or equal to one at decision block 220, the second treatment plan ($P_{GTV}$) my be utilized at process block 222. If the tracking confidence parameter $\mu_C$ does not have a value greater than or equal to one at decision block 220, the processor may return to decision block 212 to reassess the value of the tracking confidence parameter $\mu_C$. Thus, the described method may be used to adjust treatment margins in real-time, as well as reduce treatment margins during radiotherapy while safeguarding against patient dependent tracking performance drops since it is possible to restore ITV coverage as necessary. The real-time personalized treatment margins can maximize sparing of normal tissue and enable dose escalation, thereby improving treatment outcomes.

Figure 4:
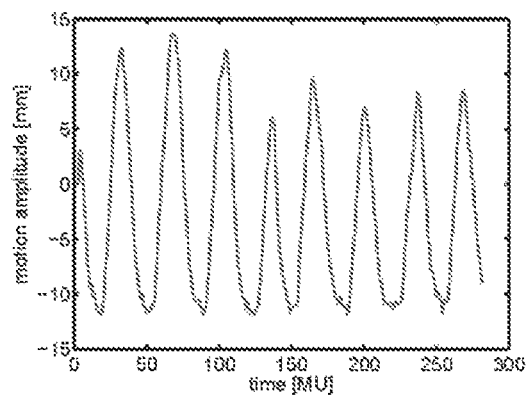
FIG. 4 is a graph showing an amplitude of tumor motion being delivered over time.

In one non-limiting example, to demonstrate the above described method, a 3D-printed tumor model (about 2×2×2 cm³ in size) from a patient's CT is placed on a slab of solid water and represents the target for motion mitigation. A dynamic motion phantom may be used to move the slab on a breathing trajectory recorded from a patient treatment. The delivered tumor motion is shown in FIG. 4 and has a peak-to-peak amplitude of about 25 mm over 300 MU.

Figure 5:
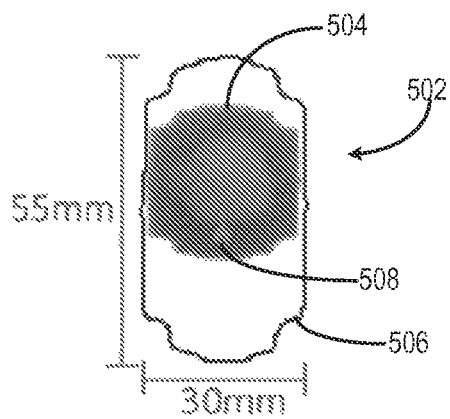
FIG. 5 shows an example EPID image of a gross target volume ($P_{GTV}$) planning aperture and an internal target volume ($P_{ITV}$) aperture.
Figures 6A, 6B:
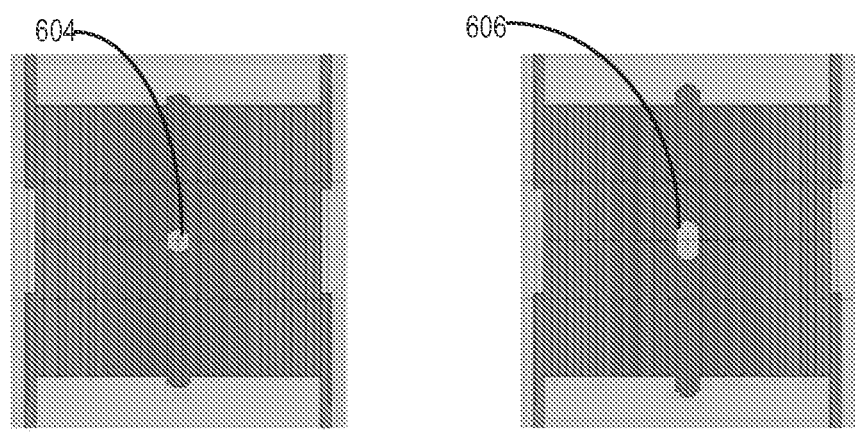
FIGS. 6A and 6B show MLC-leaf configurations for the $P_{GTV}$ aperture and the $P_{ITV}$ aperture, respectively, of FIG. 5.

A markerless beams-eye-view dynamic MLC tracking implementation developed for the Varian-C series platform of clinical linear accelerators may be utilized. The soft tissue localization algorithm (STiL) may be used to estimate soft tissue motion from continuously acquired EPID images in real-time. The STiL algorithm may also be utilized to freeze tumor motion within the treatment aperture using DMLC tracking. For example, as shown in FIG. 5, an example EPID image 502 of a $P_{GTV}$ aperture 504 during tracking is shown. Contour of a $P_{ITV}$ aperture 506 is overlaid in FIG. 5 for reference. The $P_{GTV}$ aperture 504 and the $P_{ITV}$ aperture 506 of FIG. 5 may correspond to the MLC-leaf configurations for a $P_{GTV}$ aperture 604 and a $P_{ITV}$ aperture 606, respectively, as shown in FIGS. 6A and 6B.

Returning to FIG. 5, resulting target positions 508 $p(t_i)$ that indicate the tumor model amplitude may be acquired from the EPID image 502 and fed into a linear prediction filter. The forward predicted position $\hat{p}(t_i-\delta t_s)$ may be sent along with the tracking confidence parameter $\mu_C(t)$ to the MLC component 24 which calculates and then requests the new leaf-positions by communication with the MLC controller 26.

300 MU at a dose rate of 600 MU/min may be delivered to the moving phantom representative for a typical lung SBRT treatment field. Gafchromic film (EBT3) may be fixed under the slab of solid water to visualize the delivered dose in the tumor model's frame of reference. The exit fluence of the treatment beam may be captured with the EPID 16 operated in cine mode at a frame rate of 10 Hz, for example. In some embodiments, the EPID imaging frequency may be set to 12.9 Hz to monitor the tumor in real-time. These images are utilized to derive the required real-time target position input for the aperture tracking and to monitor time resolved target and aperture location, as well as aperture size. The linear prediction filter is used to limit the impact of system latencies.

Figure 7:
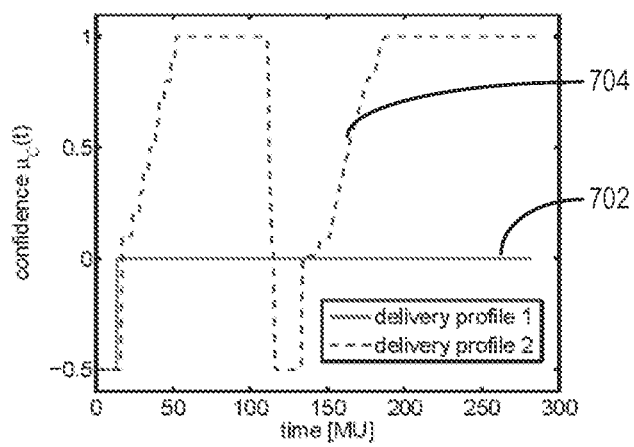
FIG. 7 is a graph showing a first confidence parameter profile and a second confidence parameter profile over time.
Figure 8A:
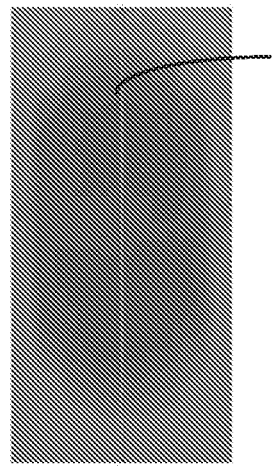
FIG. 8A shows an example image of a EBT3 film strip of the first confidence parameter profile of FIG. 7.
Figure 8B:
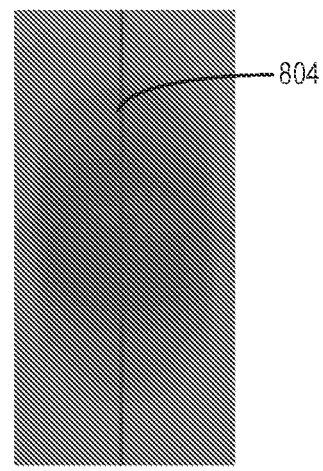
FIG. 8B shows an example image of a EBT3 film strip of the second confidence parameter profile of FIG. 7.

Turning now to FIG. 7, a first confidence parameter profile ($\mu_C(t)$) 702 to be delivered is shown with zero confidence (e.g., because of localization uncertainties on the order of the tumor motion range) and a second confidence parameter profile ($\mu_C(t)$) 704 to be delivered is shown with intermittent confidence loss. Both confidence parameter profiles 702, 704 are shown in FIG. 7 as a function of actually delivered monitor units. In one non-limiting example, the delivered dose to the tumor model and its surrounding area may be visualized with EBT3 Gafchromic film. As shown in FIG. 8A, an EBT3 film strip 802 of the first confidence parameter profile 702 is shown. Similarly, FIG. 8B shows an EBT3 film strip 804 of the second confidence parameter profile 704.

Figure 9:
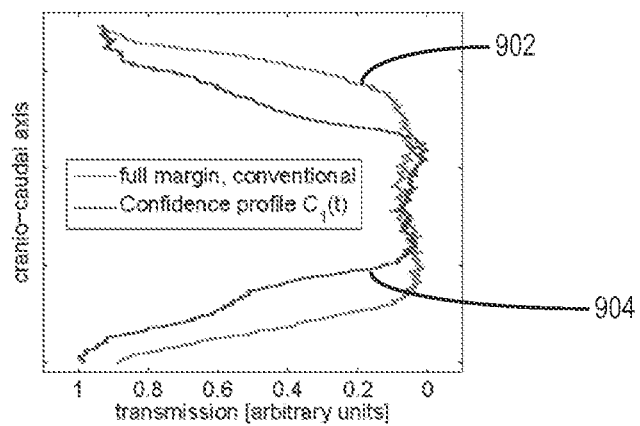
FIG. 9 is a graph showing cranio-caudal line profiles of the first and second confidence parameter profiles of FIG. 7 over time.

Turning to FIG. 9, a cranio-caudal line profile 902 corresponding to the first confidence parameter profile 702, and a cranio-caudal line profile 904 corresponding to the second confidence parameter profile 704 are shown to illustrate the effect of delivered dose reduction in healthy tissues adjacent to the target.

While reducing treatment margins in real-time was demonstrated in this study with DMLC tracking based on MV markerless tracking, the proposed concept of dynamic safeguarding does not rely on these techniques. The target positions p(t) may be estimated by any suitable imaging modality including, but not limited to, kV imaging, MV imaging, MR imaging with or without markers, and the like. Likewise, any suitable motion mitigation technique that can freeze tumor motion in beams-eye-view may achieve a similar effect.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for real-time treatment margin modification for use in radiotherapy treatment of a tumor of a subject, the method comprising:

acquiring image data from the tumor of the subject using an imaging system;

processing using a processor in communication with the imaging system, the image data;

generating a first treatment plan for radiation therapy having a first set of treatment margins based on an internal target volume (ITV) of the processed image data, the ITV encompassing an observed tumor motion range;

generating a second treatment plan for radiation therapy having a second set of treatment margins based on a contour of a gross tumor volume (GTV) of the same processed image data used to generate the first treatment plan; and during delivery of the radiotherapy treatment to the subject in real-time:

calculating a tracking confidence parameter dependent on a confidence level in at least one of target localization or motion mitigation;

selecting the first treatment plan when the tracking confidence parameter is below a first predetermined threshold;

selecting the second treatment plan when the tracking confidence parameter is above a second predetermined threshold;

generating and selecting a third treatment plan for radiation therapy having a third set of treatment margins between the first set of treatment margins and the second set of treatment margins when the tracking confidence parameter is between the first predetermined threshold and the second predetermined threshold; and communicating a selected one of the first treatment plan, the second treatment plan, or the third treatment plan.

2. The method of claim 1, wherein the second set of treatment margins is smaller than the first set of treatment margins.

3. The method of claim 1, further comprising utilizing a 4D planning approach for intra-fractional motion based on at least one of 4DCT or 4D MR images to generate the first treatment plan.

4. The method of claim 1, wherein generating the first treatment plan includes generating the first set of treatment margins representative of a current standard of care.

5. The method of claim 1, wherein generating the second treatment plan includes generating the second set of treatment margins based on an assumption of negligible intra-fractional target motion due to successful motion mitigation.

6. The method of claim 1, further comprising disabling motion mitigation when the tracking confidence parameter is below the first predetermined threshold.

7. The method of claim 1, further comprising enabling motion mitigation when the tracking confidence parameter is above the first predetermined threshold.

8. The method of claim 1, wherein the first, second and third set of treatment margins each correspond with at least one leaf position of a multi-leaf collimator (MLC) for delivering radiation to the tumor.

9. The method of claim 8, further comprising generating the third set of treatment margins by applying a linear interpolation of the at least one leaf position of the first set of treatment margins and the second set of treatment margins.

10. The method of claim 9, further comprising weighting the at least one leaf position of the first treatment margin and the second treatment margin by the tracking confidence parameter when the tracking confidence parameter is between the first predetermined threshold and the second predetermined threshold.

11. The method of claim 1, further comprising operating a radiotherapy system according to the selected one of the first treatment plan, the second treatment plan, or the third treatment plan.

12. A system for real-time treatment margin modification for use in radiotherapy treatment of a tumor of a subject comprising:
   an imaging system configured to acquire image data from the tumor of the subject;
   a processor in communication with the imaging system, the processor configured to:
      process the image data from the tumor of the subject acquired by the imaging system;
      generate a first treatment plan for radiation therapy having a first set of treatment margins based on an internal target volume (ITV) of the processed image data, the ITV encompassing an observed tumor motion range; and
      generate a second treatment plan for radiation therapy having a second set of treatment margins based on a contour of a gross tumor volume (GTV) of the same processed image data used to generate the first treatment plan; and
      during delivery of the radiotherapy treatment to the subject in real-time:
      calculate a tracking confidence parameter dependent on a confidence level in at least one of target localization or motion mitigation;
      select the first treatment plan when the tracking confidence parameter is below a first predetermined threshold;
      select the second treatment plan when the tracking confidence parameter is above a second predetermined threshold;
      generate and select a third treatment plan for radiation therapy having a third set of treatment margins between the first set of treatment margins and the second set of treatment margins when the tracking confidence parameter is between the first predetermined threshold and the second predetermined threshold; and
      communicate the selected one of the first treatment plan, the second treatment plan, or the third treatment plan to a radiotherapy system to perform the radiation therapy treatment.

13. The system of claim 12, wherein the second set of treatment margins is smaller than the first set of treatment margins.

14. The system of claim 12, wherein a 4D planning approach is utilized for intra-fractional motion based on at least one of 4DCT or 4D MR images to generate the first treatment plan.

15. The system of claim 12, wherein the first treatment plan includes the first set of treatment margins representative of a current of standard care.

16. The system of claim 12, wherein the second treatment plan includes the second set of treatment margins generated based on an assumption of negligible intrafractional target motion due to successful motion mitigation.

17. The system of claim 12, wherein when the tracking confidence parameter is below the first predetermined threshold, motion mitigation is disabled.

18. The system of claim 12, wherein when the tracking confidence parameter is above the first predetermined threshold, motion mitigation is enabled.

19. The system of claim 12, wherein the first, second and third set of treatment margins each correspond with at least one leaf position of a multi-leaf collimator (MLC) for delivering radiation to the tumor.

20. The system of claim 19, wherein the third set of treatment margins is generated by applying a linear interpolation of the at least one leaf position of the first set of treatment margins and the second set of treatment margins.

21. The system of claim 20, wherein when the tracking confidence parameter is between the first predetermined threshold and the second predetermined threshold, the at least one leaf position of the first treatment margin and the second treatment margin is weighted by the tracking confidence parameter.

* * * * *